(12) United States Patent
Okawa

(10) Patent No.: US 6,407,275 B2
(45) Date of Patent: Jun. 18, 2002

(54) METHOD FOR SYNTHESIZING 1,3-DIHYDROXYTETRAMETHYLDISILOXANE

(75) Inventor: Tadashi Okawa, Chiba Prefecture (JP)

(73) Assignee: Dow Corning Toray Silicone Co., Ltd., Tokyo (JP)

( * ) Notice: Subject to any disclaimer, the term of this patent is extended or adjusted under 35 U.S.C. 154(b) by 0 days.

(21) Appl. No.: 09/790,022

(22) Filed: Feb. 21, 2001

(30) Foreign Application Priority Data

Apr. 14, 2000 (JP) .................................... 2000-113942

(51) Int. Cl.$^7$ .................................................. C07F 7/08
(52) U.S. Cl. ........................................ 556/450; 556/459
(58) Field of Search .......................................... 556/450

(56) References Cited

U.S. PATENT DOCUMENTS 4,497,943 A * 2/1985 Takago et al. .......... 556/450 X
4,762,937 A * 8/1988 Ottlinger et al. ............. 556/459
5,057,620 A * 10/1991 Inoue et al. ................. 556/459

FOREIGN PATENT DOCUMENTS

JP          7-224072            8/1995

* cited by examiner

*Primary Examiner*—Paul F. Shaver
(74) *Attorney, Agent, or Firm*—Melvin D. Fletcher

(57) ABSTRACT

A method for synthesizing 1,3-dihydroxytetramethyldisiloxane comprising effecting the hydrolytic dehydrogenation of 1,1,3,3-tetramethyldisiloxane in the presence of water and a transition metal catalyst from Group VIII of the long-period form of the Periodic Table.

4 Claims, No Drawings

METHOD FOR SYNTHESIZING 1,3-DIHYDROXYTETRAMETHYLDISILOXANE

FIELD OF THE INVENTION

This invention is a method for synthesizing 1,3-dihydroxytetramethyldisiloxane. More particularly, this invention is a high-yield method for synthesizing high-purity 1,3-dihydroxytetramethyldisiloxane from 1,1,3,3-tetramethyldisiloxane.

BACKGROUND OF THE INVENTION 1,3-Dihydroxytetramethyldisiloxane is important as a starting material for dimethylpolysiloxanes. The following methods are known for its synthesis:

(1) hydrolytic dehydrochlorination of 1,3-dichlorotetramethyldisiloxane in the presence of gaseous ammonia while regulating the pH of the water (*J. Am. Chem. Soc.*, 74, 5225 (1952));

(2) hydrolytic dehydrochlorination of 1,3-dichlorotetramethyldisiloxane in water-diethyl ether in the presence of pyridine (*Macromolecules*, 20, 2345 (1987));

(3) hydrolytic dehydrochlorination of 1,3-dichlorotetramethyldisiloxane in water-diethyl ether in the presence of ammonium carbonate (*J. Chem. Soc.*, 5978 (1963); *J. Organomet. Chem.*, 453, 13 (1993)); and (4) hydrolytic dehydrochlorination of 1,3-dichlorotetramethyldisiloxane in a homogeneous water-alcohol mixed solvent that contains a hydrogen chloride scavenger (Japanese Patent Application Hei 7-224072).

All of these synthesis methods start from 1,3-dichlorotetramethyldisiloxane. However, the acquisition of this disiloxane starting material is highly problematic because it cannot be directly synthesized by the direct process for the synthesis of dimethyldichlorosilane (precursor for dimethylpolysiloxanes). In addition, each of the foregoing synthesis methods suffers from its own particular problem. Thus, synthesis method (1) requires long reaction times and hence suffers from a very poor productivity. Pyridine hydrochloride, which is problematic both in terms of disposal and recovery, is produced as a by-product in synthesis method (2). Synthesis method (3) requires the use of unstable ammonium carbonate. In the case of synthesis method (4), alcohol is mixed in the wastewater, which increases the chemical oxygen demand of the wastewater. Another problem with the methods under discussion is that the very high reactivity of the 1,3-dihydroxytetramethyldisiloxane product makes it quite prone to undergo condensation in the presence of an acid or base catalyst. This condensation results in the production of cyclic dimethylsiloxanes and silanol-endblocked dimethylsiloxane oligomers and polymers, which lowers the yield and purity of the 1,3-dihydroxytetramethyldisiloxane product.

In another vein, the dimethylchlorosilane generated as a by-product in the direct method for synthesizing dimethyldichlorosilane (precursor for dimethylpolysiloxanes) has few uses. Moreover, the 1,1,3,3-tetramethyldisiloxane afforded by the hydrolysis of dimethylchlorosilane also has few uses, and applications for this disiloxane have been desired.

In specific terms, the object of this invention is to provide a high-yield method for synthesizing high-purity 1,3-dihydroxytetramethyldisiloxane from 1,1,3,3-tetramethyldisiloxane, which can itself be produced by hydrolysis of the dimethylchlorosilane produced as a by-product in the direct process for making dimethyldichlorosilane.

SUMMARY OF THE INVENTION

The present invention is a method for synthesizing 1,3-dihydroxytetramethyldisiloxane. The method comprises effecting the hydrolytic dehydrogenation of 1,1,3,3-tetramethyldisiloxane in the presence of water and a transition metal catalyst from Group VIII of the long-period form of the Periodic Table.

DESCRIPTION OF THE INVENTION

The present invention is a method for synthesizing 1,3-dihydroxytetramethyldisiloxane. The method comprises effecting the hydrolytic dehydrogenation of 1,1,3,3-tetramethyldisiloxane in the presence of water and a transition metal catalyst from Group VIII of the long-period form of the Periodic Table.

1,1,3,3-Tetramethyldisiloxane is the starting material for the present method. This compound is readily obtained by hydrolysis of the dimethylchlorosilane that is produced as a by-product in the direct process for synthesizing dimethyldichlorosilane (precursor for dimethylpolysiloxanes). This 1,1,3,3-tetramethyldisiloxane can therefore be acquired more easily and cheaply than 1,3-dichlorotetramethyldisiloxane.

The catalyst used in the present method is a transition metal catalyst from Group VIII of the long-period form of the Periodic Table. This catalyst promotes or accelerates the hydrolytic dehydrogenation of the 1,1,3,3-tetramethyldisiloxane and can be exemplified by platinum catalysts such as platinum black powder, platinum supported on silica powder, platinum supported on alumina powder, platinum supported on carbon powder (e.g., activated carbon), chloroplatinic acid, 1,3-divinyltetramethyldisiloxane complexes of platinum, carbonyl complexes of platinum, and olefin complexes of platinum; by palladium catalysts such as palladium supported on silica powder, palladium supported on alumina powder, palladium supported on carbon powder (e.g., activated carbon), carbonyl complexes of palladium, and olefin complexes of palladium; and by rhodium catalysts such as rhodium supported on silica powder, rhodium supported on alumina powder, rhodium supported on carbon powder (e.g., activated carbon), carbonyl complexes of rhodium, and olefin complexes of rhodium. Preferred catalysts take the form of a transition metal (e.g., platinum, palladium, rhodium) supported on a powder such as alumina, silica, or carbon. Palladium supported on carbon powder is particularly preferred for use as the catalyst in the present method.

While the amount of catalyst used in the present method is not critical, in general the catalyst is preferably used in an amount that provides from 0.0001 to 1 gram catalytic metal per equivalent of silicon-bonded hydrogen in the 1,1,3,3-tetramethyldisiloxane.

Water should be used in the present method in at least a stoichiometric amount, but its quantity of addition is not otherwise critical. However, the addition of large amounts of water results in phase separation of the reaction solution, even with the use of a solvent compatible with water, and slows the reaction rate in addition to making removal of the water post-reaction much more difficult. These considerations make it preferable to add water in the minimum required amount. In specific terms, the addition of water in an amount that provides from 1- to 2-fold equivalents of water with respect to the silicon-bonded hydrogen in the 1,1,3,3-tetramethyldisiloxane enables conversion of the silicon-bonded hydrogen in the 1,1,3,3-tetramethyldisiloxane to silanol with an almost complete absence of secondary reactions.

Solvent is preferably used in the present method for the purpose of achieving a good intermixing of the water and starting 1,1,3,3-tetramethyldisiloxane. This solvent preferably exhibits affinity for the water, 1,1,3,3-tetramethyldisiloxane, and 1,3-dihydroxytetramethyldisiloxane, and is exemplified by ethers such as diethyl ether, dioxane, and tetrahydrofuran; ketones such as acetone, methyl ethyl ketone, and methyl isobutyl ketone; alcohols such as methanol, ethanol, and isopropanol; and esters such as methyl acetate, ethyl acetate, and methyl propionate.

The hydrolytic dehydrogenation of 1,1,3,3-tetramethyldisiloxane can be conducted in the present method by mixing the 1,1,3,3-tetramethyldisiloxane, water, Group VIII transition metal catalyst, and optional solvent. Given the desirability from a safety standpoint of avoiding the generation of large amounts of the hydrogen by-product all at once, this mixing is preferably carried out by the gradual dropwise addition under an inert gas atmosphere (e.g., argon, nitrogen) of the 1,1,3,3-tetramethyldisiloxane to a mixture of the water, Group VIII transition metal catalyst, and optional solvent.

The reaction conditions are not particularly critical for the present method, but the reaction temperature preferably is in the range from 10 to 100° C. and the reaction time is generally preferably from 10 minutes to 5 hours. The progress of the reaction can be followed by infrared spectroscopic monitoring of the reaction mixture for the characteristic absorption of the silicon-bonded hydrogen atom. The reaction can be regarded as finished at the point at which this characteristic absorption has disappeared. The 1,3-dihydroxytetramethyldisiloxane product can then be recovered by separation of the catalyst by a suitable method, such as adsorption on activated carbon or filtration, and elimination of the low boilers by, for example, distillation. The purity of the disiloxane can be boosted by optional recrystallization of the disiloxane from solvent.

Since the present method does not use an acidic or basic starting material and carries out the hydrolytic dehydrogenation of 1,1,3,3-tetramethyldisiloxane under almost neutral conditions, the 1,3-dihydroxytetramethyldisiloxane product does not participate in secondary reactions, such as condensation of its silanol groups. The present method therefore has the advantage of producing the subject disiloxane in high yields and at high purities. Another advantage offered by the present method is its ability to start from 1,1,3,3-tetramethyldisiloxane, which can be obtained by hydrolysis of the dimethylchlorosilane that is produced as a by-product in the direct process for the synthesis of dimethyldichlorosilane (starting material for dimethylpolysiloxanes).

The present method for synthesizing 1,3-dihydroxytetramethyldisiloxane is explained in greater detail below through a working example.

EXAMPLE 1

While operating under a nitrogen atmosphere, 10.8 g water (600 mmol), 30 g acetone, and 0.45 g of a catalyst comprising 5 weight % palladium supported on activated carbon powder (Palladium Activated Carbon from Wako Junyaku Kogyo Kabushiki Kaisha) were introduced into a four neck flask. Then, while stirring the flask content and cooling with water, 30 g of 1,1,3,3-tetramethyldisiloxane (223.9 mmol) were added dropwise over a period of 2 hours while keeping the reaction temperature at or below 25° C. After the completion of addition, the reaction mixture was stirred for another 1.5 hours at room temperature, at which point a small amount of the reaction mixture was sampled and analyzed by infrared spectroscopy. The results confirmed that the characteristic absorption of the silicon-bonded hydrogen had disappeared. The catalyst was then filtered from the reaction mixture and the lower boilers were distilled from the filtrate by heating at 40° C. under reduced pressure. 35.3 g Of colorless crystals were obtained (crude yield=95%). This product was recrystallized from hexane to give 27.8 g colorless crystals (yield=75%). Analysis of this recrystallized product by nuclear magnetic resonance spectroscopy confirmed it to be 1,3-dihydroxytetramethyldisiloxane. A purity of 99.6% was also confirmed. The remaining 0.4% was determined to be 1,7-dihydroxyoctamethyltetrasiloxane, which had been produced by the condensation of 1,3-dihydroxytetramethyldisiloxane.

I claim:
1. A method for synthesizing 1,3-dihydroxytetramethyldisiloxane comprising effecting the hydrolytic dehydrogenation of 1,1,3,3-tetramethyldisiloxane in the presence of water and a transition metal catalyst from Group VIII of the long-period form of the Periodic Table.

2. The method of claim 1, where the transition metal catalyst is a palladium catalyst.

3. The method of claim 1, where the transition metal catalyst is carbon powder-supported palladium.

4. The method of claim 1, where the 1,1,3,3-tetramethyldisiloxane is a hydrolysis product of dimethylchlorosilane obtaining as a by-product from the direct process for synthesis of dimethyldichlorosilane.

* * * * *